United States Patent
Kim et al.

(10) Patent No.: US 6,713,228 B2
(45) Date of Patent: Mar. 30, 2004

(54) ETHER MONOMERS AND POLYMERS HAVING MULTI-RING STRUCTURES, AND PHOTOSENSITIVE POLYMERS AND RESIST COMPOSITIONS OBTAINED FROM THE SAME

(75) Inventors: Hyun-Woo Kim, Kyungki-do (KR); Sang-Gyun Woo, Kyungki-do (KR); Sung-Ho Lee, Kyungki-do (KR)

(73) Assignee: Samsung Electronics Co., Ltd., Suwon (KR)

( * ) Notice: Subject to any disclaimer, the term of this patent is extended or adjusted under 35 U.S.C. 154(b) by 131 days.

(21) Appl. No.: 10/132,804

(22) Filed: Apr. 24, 2002

(65) Prior Publication Data
US 2002/0160303 A1 Oct. 31, 2002

(30) Foreign Application Priority Data
Apr. 25, 2001 (KR) .......................... 2001-22356

(51) Int. Cl.[7] .................. G03F 7/039; C08F 34/02
(52) U.S. Cl. ................ 430/270.1; 430/907; 430/910; 430/905; 525/242; 525/245; 525/247; 525/268; 549/386
(58) Field of Search ............... 430/270.1, 905, 430/910, 907; 525/242, 245, 247, 268; 549/386

(56) References Cited
U.S. PATENT DOCUMENTS 5,380,659 A * 1/1995 Holla et al. ............... 435/196
6,517,990 B1 * 2/2003 Choi et al. ............... 430/270.1
2002/0072009 A1 * 6/2002 Kim et al. ............... 430/270.1
2002/0146642 A1 * 10/2002 Kim et al. ............... 430/270.1

* cited by examiner

*Primary Examiner*—Janet Baxter
*Assistant Examiner*—Yvette C. Thornton
(74) *Attorney, Agent, or Firm*—Marger Johnson & McCollom, P.C.

(57) ABSTRACT

Provided are alkenyl ether-based monomers having multi-ring structure, and photosensitive polymers and resist compositions obtained from the same. The photosensitive polymer includes a monomer unit represented by the following formula:

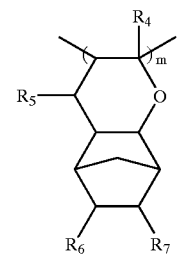

wherein $R_4$ and $R_5$ are independently -H or -$CH_3$, and $R_4$ are independently -H, -OH or a alkyl group having 1–20 carbon atoms.

61 Claims, No Drawings

ETHER MONOMERS AND POLYMERS HAVING MULTI-RING STRUCTURES, AND PHOTOSENSITIVE POLYMERS AND RESIST COMPOSITIONS OBTAINED FROM THE SAME

BACKGROUND OF THE INVENTION

1. Field of the Invention

The present invention relates to a polymer and a resist composition that can be used as an electronic industrial material such as photoresist, and more particularly, to monomers having multi-ring structure, and a photosensitive polymer and a resist composition obtained from the same.

2. Description of the Related Art

As the manufacture of semiconductor devices becomes complicated and the integration density of semiconductor devices highly increases, there is a need to form a fine pattern. Furthermore, with regard to 1-Gigabit or more semiconductor devices, a pattern size having a design rule of 0.15 μm or less is needed. However, when a conventional photoresist material is exposed with KrF excimer laser (248 nm), there is a limitation in forming such a fine pattern. For this reason, development of a lithography technique using a new exposure light source, ArF excimer laser (193 nm), is under way to be commercially available in the near future. Also, for adoption to the manufacture of semiconductor devices in which formation of patterns of 0.15 μm or less is needed, research into another next-generation technique using $F_2$ excimer laser (157 mn) as a new exposure light source is being extensively conducted.

Whereas research into ArF and $F_2$ excimer laser techniques is being vigorously carried out, existing resist compositions suitable for use in those techniques cause many problems in practical use, compared to conventional KrF resist compositions. Almost all well-known ArF resist compositions contain (meth)acryl-based polymers. Among these polymers, a methacrylate copolymer having an alicyclic protecting group, which is expressed by the formula below:

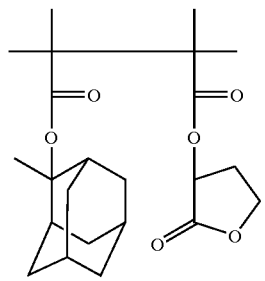

This polymer has an adamantyl group, which contributes to enhancing resistance to dry etching, and a lactone group, which improves adhesiveness, in its methacrylate backbone. As a result, the resolution of the resist and the depth of focus has improved. However, resistance to dry etching is still weak, and serious line edge roughness is observed after line patterns are formed from the resist layer.

Another drawback of the polymer having the formula above is that the raw material used to synthesis the polymer is expensive.

As another conventional resist composition, a cycloolefin-maleic anhydride (COMA) alternating polymer having the following formula has been suggested:

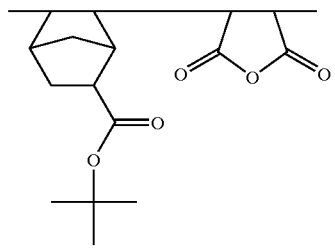

In the production of copolymer, such as a COMA alternating polymer having the formula above, resistance to dry etching is improved and the production cost of raw material is cheap, whereas resolution of the polymer sharply decreases. Also, the copolymer has a glass transition temperature (Tg) of 200° C. or higher due to the structural strength of norbornene contained in the backbone, resulting in processing difficulty. In addition, the synthetic polymers have in their backbone the alicyclic group, which shows prominent hydrophobicity, and thus the adhesiveness to neighboring material layers is very poor.

To overcome the-described problems, in recent years, polymers having various structures have been proposed, the polymers exemplified by a copolymer of a COMA system and a monomer units having a (meth)acylate-based backbone:

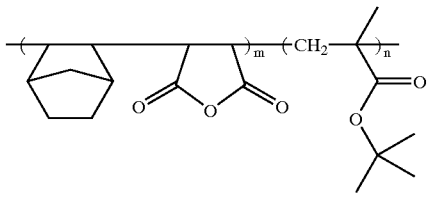

Since the copolymer having the above structure has a glass transition temperature (Tg) lower than that of the COMA system, the processing can be easily carried out. Also, since a polarity change occurs to (meth)acrylate monomer units, increased resolution can be achieved. However, according to reports hitherto made, resistance to dry etching has not been enhanced very much. To increase the resistance to dry etching, a bulky protecting group such as an adamantly group, rather than a t-butyl group, is introduced to the above structure. However, the resulting resist still exhibits weak resistance to dry etching or poor patterns.

As the pattern rule becomes finer in the manufacture of semiconductor devices, the aspect ratio is considerably increased, resulting in the collapse of patterns. To avoid this, a lithography technique using ArF excimer lasers may be used. However, in the case of using the lithography technique using ArF excimer lasers, patterns must be formed such that a resist layer is coated on a wafer to a thickness of 4000 A or less. As the thickness of the resist layer is reduced as above, it is necessary to enhance resistance to dry etching.

Another conventional resist composition proposed for enhancing resistance to dry etching includes a polymer having only a norbornene structure in its backbone, represented by the following formula:

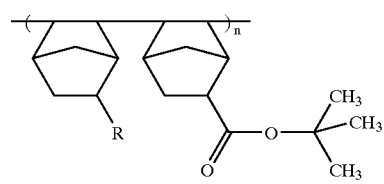

However, in order to obtain the above structure, a catalyst made from a heavy metal such as platinum or nickel is necessary. The heavy metal used as a catalyst during polymerization cannot be completely removed. Thus, the resist composition obtained from the polymer may cause serious contamination due to the heavy metal, making practical use difficult.

SUMMARY OF THE INVENTION

To solve the above problems, it is a first object of the present invention to provide monomers used as raw materials for polymers that can be adopted to various light sources including KrF excimer lasers, ArF excimer lasers or $F_2$ excimer lasers in a photolithography process.

It is a second object of the present invention to provide a photosensitive polymer which can be obtained by a simple synthesis method and can provide enhanced resistance to dry etching without contamination due to a heavy metal catalyst.

It is a third object of the present invention to provide a resist composition having enhanced resistance to dry etching and good transmittance, can adopt various light sources including KrF excimer lasers, ArF excimer lasers or $F_2$ excimer lasers in a photolithography process and can provide a good lithographic property of high resolution.

The first object of the present invention can be accomplished by providing a monomer having a structure represented by the following formula:

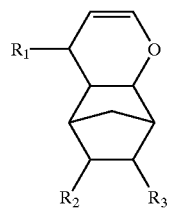

wherein $R_1$ is -H or -$CH_3$, $R_2$ and $R_3$ are -H, -OH or an alkyl group having 1–20 carbon atoms. In the monomer according to the present invention, $R_2$ and $R_3$ are preferably selected from a group consisting of alkyl, hydroxyalkyl, alkyloxy, carboxyl, carbonyl, ester, and fluorinated alkyloxy.

Preferably, the monomer has a structure represented by the following formula:

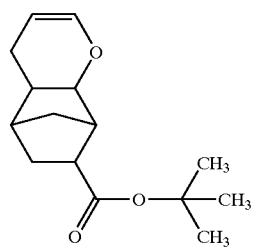

Also, the monomer preferably has a structure represented by the following formula:

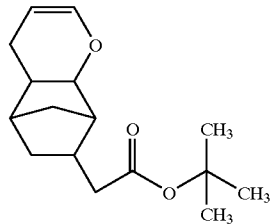

The monomer may have a structure represented by the following formula:

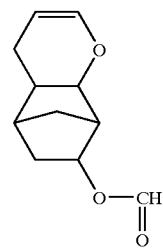

Also, the monomer may have a structure represented by the following formula:

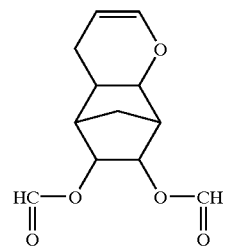

Further, the monomer may have a structure represented by the following formula:

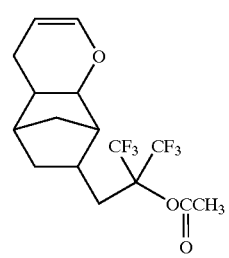

To achieve the second object, there is provided a photosensitive polymer comprising a monomer unit represented by the following formula:

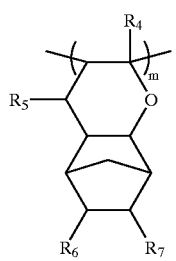

wherein R4 and R$_5$ are -H or -CH$_3$, and R$_6$ and R$_7$ are -H1 -OH or an alkyl group containing 1–20 carbon atoms.

In a preferred photosensitive polymer, at least one of R$_6$ and R$_7$ is selected from a group consisting of alkyl, hydroxyalkyl, alkyloxy, carboxyl, carbonyl, ester and fluorinated alkyloxy.

Preferably, the photosensitive polymer has a structure represented by the following formula:

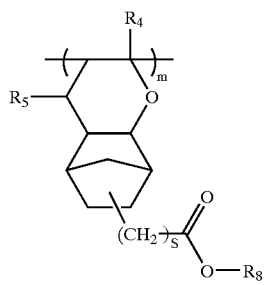

wherein R$_8$ is an alkyl group having 4–12 carbon atoms, and s is an integer from 0 to 2, preferably 1 to 2.

More preferably, R$_8$ is one of t-butyl, tetrahydropyranyl or a substituted or unsubstituted alicyclic group. Examples of R$_8$ is selected from a group consisting of 1-methyl-1-cyclohexyl, 1-ethyl-1-cyclohexyl, 2-methyl-2-norbomyl, 2-ethyl-2-norbornyl, 2-methyl-2-isobomyl, 2-ethyl-2-isobomyl, 8-methyl-8-tricyclo[5.2.1.0$^{2,6}$]decanyl, 8-ethyl-8-tricyclo [5.2.1.0$^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl.

Also, the photosensitive polymer preferably has a structure represented by the following formula:

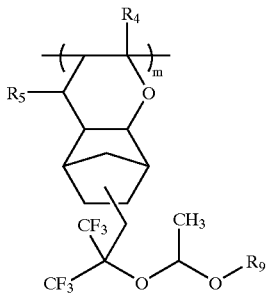

wherein R$_9$ is a C$_1$~C$_{20}$ hydrocarbon group.

In the above formula, R$_9$ is selected from a group consisting of methyl, ethyl, a t-butyl and cyclohexyl.

Preferably, the photosensitive polymer has a structure represented by the following formula:

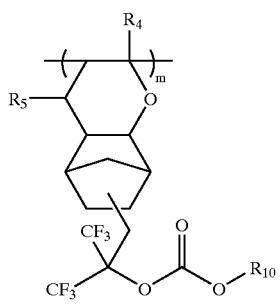

wherein R$_{10}$ is selected from a group consisting of methyl, ethyl, t-butyl and cyclohexyl, Also, the photosensitive polymer preferably has a structure represented by the following formula:

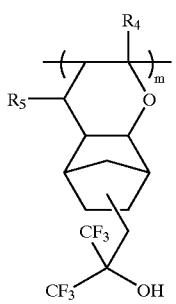

According to another aspect of the present invention, there is provided a photosensitive polymer having a structure represented by the following formula:

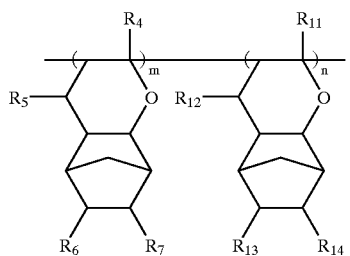

wherein R$_4$, R$_5$, R$_{11}$ and R$_{12}$ are -H or -CH$_3$, R$_6$, R$_7$, R$_{13}$ and R$_{14}$ are -H, -OH or alkyl group having 1–30 carbon atoms, at least one of R$_6$, R$_7$, R$_{13}$ and R$_{14}$ is an acid-labile group, and m/(m+n) is from about 0.1 to 0.9.

In the photosensitive polymer, at least one of R$_6$, R$_7$, R$_{13}$ and R$_{14}$ is preferably selected from a group consisting of alkyl, hydroxyalkyl, alkyloxy, carboxyl, carbonyl, ester and fluorinated alkyloxy.

Preferably, the photosensitive polymer has a structure represented by the following formula:

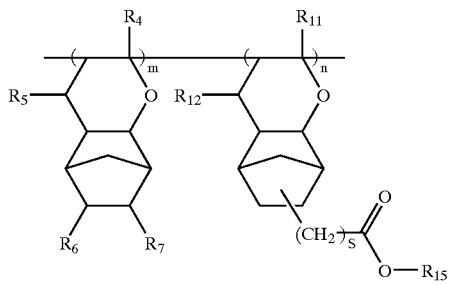

wherein $R_{15}$ is an alkyl group having 4–12 carbon atoms and s is an integer of from 0 to 2, preferably 1 to 2. More preferably, $R_{15}$ is selected from a group consisting of t-butyl, tetrahydropyranyl, and a substituted or unsubstituted alicyclic hydrocarbon havig 6–12 carbon atoms. Examples of $R_{15}$ is selected from a group consisting of 1-methyl-l-cyclohexyl, 1-ethyl-l-cyclohexyl, 2-methyl-2-norbomyl, 2-ethyl-2-norbomyl, 2-methyl-2-isobomyl, 2-ethyl-2-isobomyl, 8-methyl-8-tricyclo[$5.2.1.0^{2,6}$]decanyl, 8-ethyl-8-tricyclo[$5.2.1.0^{2,6}$]decanyl, 2-methyl-2-adamantyl, 2-ethyl-2-adamantyl group, 1-adamantyl-1-methylethyl, 2-methyl-2-fenchyl and 2-ethyl-2-fenchyl.

Also, the photosensitive polymer preferably has a structure represented by the following formula:

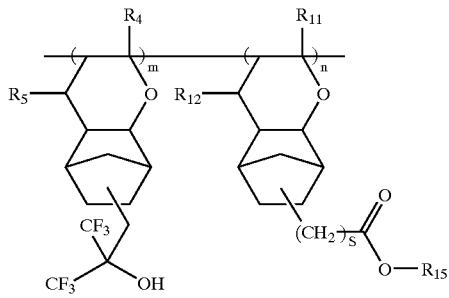

wherein $R_{15}$ is an alkyl group having 4–12 carbon atoms and s is an integer of from 0 to 2, preferably 1 to 2.

The photosensitive polymer preferably has a structure represented by the following formula:

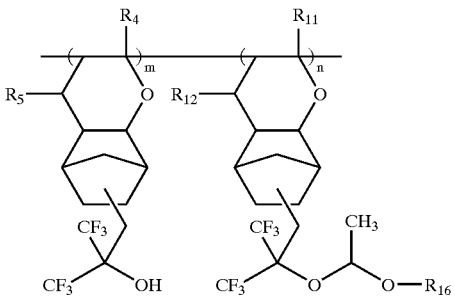

wherein $R_{16}$ is a $C_1$~$C_{20}$ hydrocarbon group. More preferably, $R_{16}$ is selected from a group consisting of methyl, ethyl, t-butyl and cyclohexyl.

Also, the photosensitive polymer preferably can have a structure represented by the following formula:

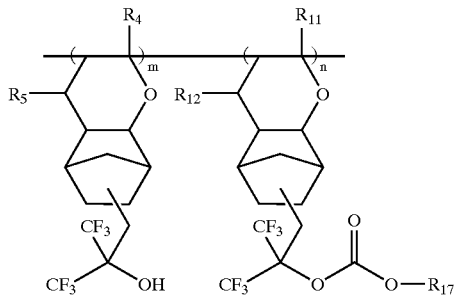

wherein $R_{17}$ is an alkyl group having from 1–20 carbon atoms. More preferably, $R_{17}$ is selected from a group consisting of methyl, ethyl, t-butyl and cyclohexyl.

According to still another aspect of the present invention, there is provided a photosensitive polymer including a polymerized product of (a) at least one monomer unit having a structure represented by the following formula:

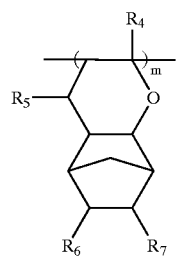

wherein $R_4$ and $R_5$ are -H or $-CH_3$, $R_6$ and $R_7$ are -H, -OH or an alkyl group having 1–20 carbon atoms, and (b) at least one comonomer selected from the group consisting of a maleic anhydride monomer, an acrylate monomer, a methacrylate monomer, a norbomene monomer, a dihydrofuran monomer and a dihydropyran monomer.

Preferably, at least one of $R_6$ and $R_7$ is selected from a group consisting of alkyl, hydroxyalkyl, alkyloxy, carboxyl, carbonyl, ester and fluorinated alkyloxy.

The comonomer unit is preferably a dihydrofuran or dihydropyran monomer unit. Here, the photosensitive polymer has a structure represented by the following formula:

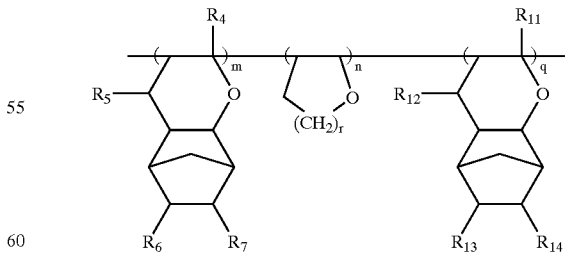

wherein r is 1 or 2, $R_{11}$ and $R_{12}$ are -H or $-CH_3$, $R_{11}$ and $Rl_4$ are -H, -OH or an alkyl group having 1–30 carbon atoms and $R_6$, $R_7$, $R_{13}$ or $R_{14}$ are an acid-labile group, and m/(m+n+q) is from about 0.1 to 0.8, n/(m+n+q) is in the range of 0.1 to 0.8, and q/(m+n+q) is in the range of 0.1 to 0.8.

In particular, the photosensitive polymer preferably has a structure represented by the following formula:

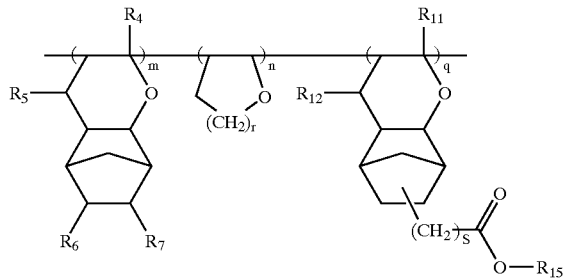

wherein $R_{15}$ is alkyl group having 4–12 carbon atoms and s is an integer of from 0 to 2, preferably 1 to 2. More preferably, $R_{15}$ is selected from a group consisting of t-butyl, tetrahydropyranyl, and a substituted or unsubstituted alicyclic hydrocarbon group having 6–12 carbon atoms.

Also, the photosensitive polymer preferably has a structure represented by the following formula:

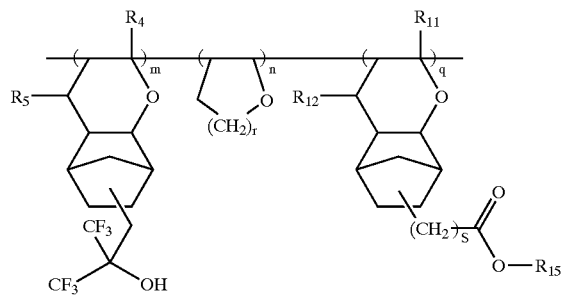

wherein $R_{15}$ is an alkyl group having 4–12 carbon atoms and s is an integer of from 0 to 2, preferably 1 to 2.

Further, the photosensitive polymer preferably has a structure represented by the following formula:

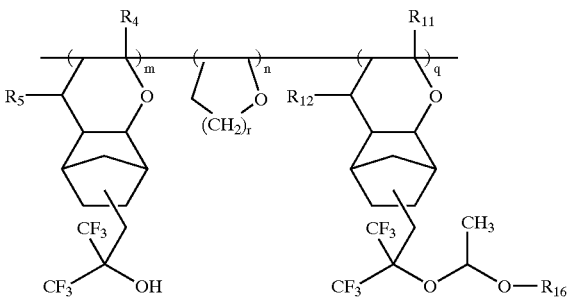

wherein $R_{16}$ is a $C_1$~$C_{20}$ hydrocarbon group. More preferably, $R_{16}$ is selected from a group consisting of methyl, ethyl, t-butyl and cyclohexyl.

Preferably, the photosensitive polymer has a structure represented by the following formula:

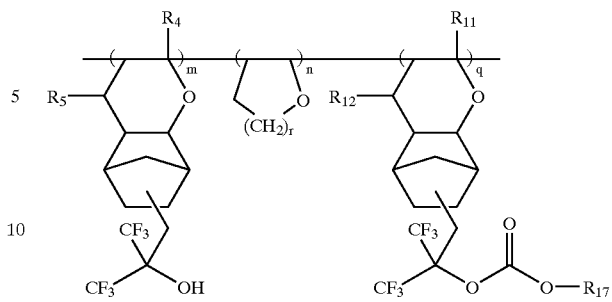

herein $R_{17}$ is an alkyl group having 1–20 carbon atoms. More preferably, $R_{17}$ is selected from a group consisting of methyl, ethyl, t-butyl and cyclohexyl.

In the photosensitive polymer, the comonomer unit preferably has a structure represented by the following formula:

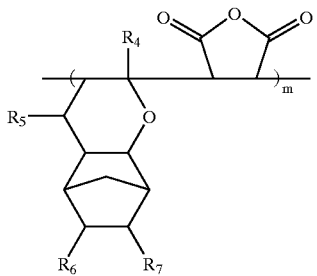

In particular, the photosensitive polymer preferably has a structure represented by the following formula:

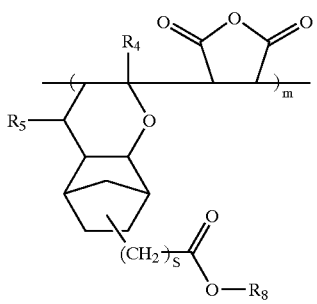

wherein $R_8$ is an alkyl group having 6–12 carbon atoms and s is an integer of from 0 to 2, preferably 1 to 2. $R_8$ is one of t-butyl, tetrahydropyranyl or a substituted or unsubstituted alicyclic group.

In the case where the comonomer unit is a maleic anhydride monomer unit, the photosensitive polymer preferably has a structure represented by the following formula:

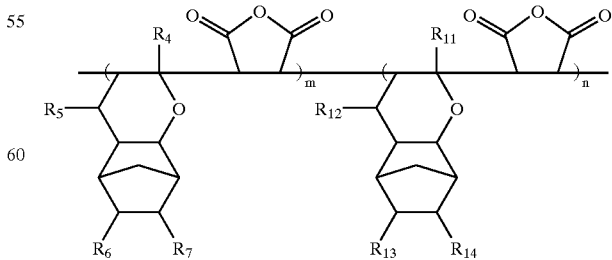

wherein $R_{11}$ and $R_{12}$ are -H or -$CH_3$, $R_{13}$ and $R_{14}$ are -H, -OH an alkyl group, at least one of $R_6$, $R_7$, $R_{13}$ and $R_{14}$ is an acid-labile group, m/(m+n) is in the range of 0.1 to 0.9, and n/(m+n) is from about 0.1 to 0.9.

In particular, the photosensitive polymer has a structure represented by the following formula:

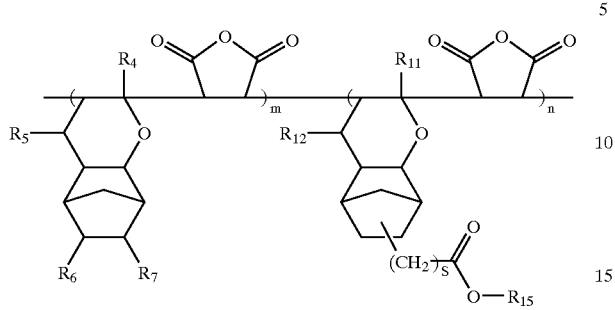

wherein $R_{15}$ is an alkyl group and s is an integer of from 0 to 2. More preferably, $R_{15}$ is selected from a group consisting of t-butyl, tetrahydropyranyl or a substituted or unsubstituted an alkyl group.

Also, the comonomer unit may include a maleic anhydride monomer unit and an acrylate or methacrylate monomer unit. Here, the photosensitive polymer preferably has a structure represented by the following formula:

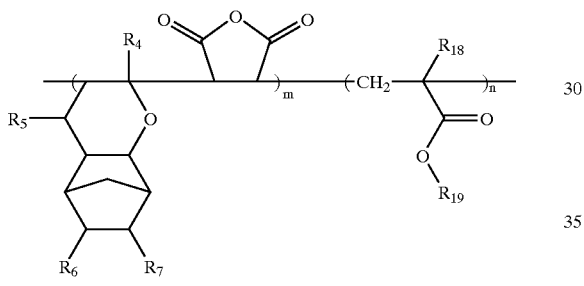

wherein $R_8$ is -H or -CH$_3$, $R_{19}$ is an acid-labile group, m/(m+n) is in the range of 0.1 to 0.9, and n/(m+n) is in the range of 0.1 to 0.9. More preferably, $R_{19}$ is one of t-butyl, a tetrahydropyranyl or a substituted or unsubstituted $C_6$~$C_{12}$ alicyclic hydrocarbon group.

Also, the comonomer unit may include a maleic anhydride monomer unit and a norbornene monomer unit. Here, the photosensitive polymer preferably has a structure represented by the following formula:

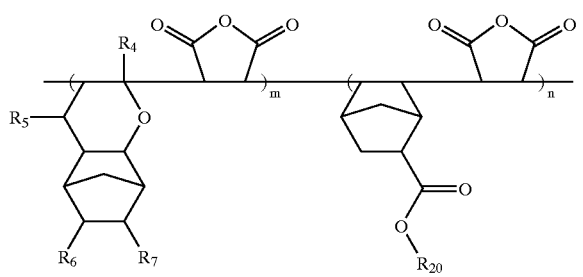

wherein $R_{20}$ is an acid-labile group, m/(m+n) is in the range of 0.1 to 0.8, and n/(m+n) is in the range of 0.1 to 0.8. More preferably, $R_{20}$ is selected from a group consisting of t-butyl, tetrahydropyranyl or a substituted or unsubstituted $C_6$~$C_{12}$ alicyclic hydrocarbon group.

The third object of the present invention can be accomplished by providing a resist composition including (a) a photosensitive polymer having a structure represented by the following formula:

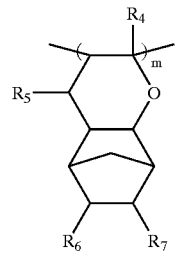

wherein $R_4$ and $R_5$ are -H or -CH$_3$, and $R_6$ and $R_7$ are -H, -OH or an alkyl group having 1–20 carbon atoms and (b) a photoacid generator (PAG). In the resist composition, $R_6$ and $R_7$ is preferably selected from a group consisting of alkyl, hydroxyalkyl, alkyloxy, carboxyl, carbonyl, ester and fluorinated alkyloxy.

Also, in the resist composition, the photosensitive polymer may have various structures as defined above.

According to another aspect of the present invention, there is provided a resist composition including (a) a photosensitive polymer comprising a polymerized product of (i) at least one monomer unit having a structure represented by the following formula:

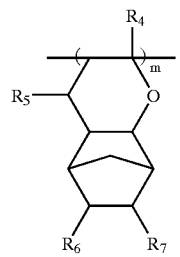

wherein $R_4$ and $R_5$ are -H or -CH$_3$, $R_6$ and $R_7$ are -H, -OH or an alkyl group containing 1–20 carbon atoms, and (ii) at least one comonomer selected from the group consisting of a maleic anhydride monomer, an acrylate or methacrylate monomer, a norbornene monomer, and dihydrofuran or dihydropyran monomer, and (b) a PAG.

In the resist composition, the photosensitive polymer may have various structures as defined above.

In the resist composition, the weight average molecular weight of the photosensitive polymer is preferably 3,000~100,000.

The amount of the PAG may 1~30 wt % on the basis of the weight of the photosensitive polymer. Preferably, the PAG includes triarylsulfonium salts, diaryliodonium salts, sulfonates, or mixtures thereof. More preferably, the PAG includes triphenylsulfonium triflate, triphenylsulfonium antimonate, diphenyliodonium triflate, diphenyliodonium antimonate, methoxydiphenyliodonium triflate, di-t-butyldiphenyliodonium triflate, 2,6-dinitrobenzyl sulfonates, pyrogallol tris(alkylsulfonates), N-hydroxysuccinimide triflate, norbornene-dicarboximide-triflate, triphenylsulfonium nonaflate, diphenyliodonium nonaflate, methoxydiphenyliodonium nonaflate, di-t-butyldiphenyliodonium nonaflate, N-hydroxysuccinimide nonaflate, norbornene-dicarboximide-nonaflate, PFOS (triphenylsulfonium perfluorooctanesulfonate), diphenyliodonium PFOS, methoxydiphenyliodonium PFOS, di-t-butyldiphenyliodonium triflate, N-hydroxysuccinimide PFOS, norbomene-dicarboximide PFOS, or mixtures thereof. In particular, the resist composition according to the above described aspects of the present invention may further include an organic base. The amount of the organic base is preferably 0.01~2.0 wt % on the basis of the weight of the photosensitive polymer. Preferably, the organic base includes a tertiary amine compound alone or a mixture of at least two tertiary amine compounds. Examples of the organic base include triethylamine, triisobutylamine, triisooctylamine, triisodecylamine, diethanolamine, triethanolamine, N-alkyl substituted pyrrolidinone, N-alkyl substituted caprolactam, N-alkyl substituted valerolactam, or a mixture thereof. The resist composition according to the above described aspects of the present invention may further include a surfactant of 30 to 200 ppm.

The photosensitive polymer according to the present invention has a structure that has enhanced resistance to dry etching and good adhesiveness to underlying layers. Also, since the photosensitive polymer according to the present invention can be obtained through cationic polymerization, a multi-ring backbone structure can be provided without contamination due to a heavy metal catalyst. Further, the photosensitive polymer included in a resist composition according to the present invention can be adopted to various light sources including KrF excimer lasers (248 nm), ArF excimer lasers (193 nm) or $F_2$ excimer lasers (157 nm). In particular, the resist composition obtained from the photosensitive polymer according to the present invention exhibits superior transmittance at 157 nm. The resist composition has enhanced resistance to dry etching and good transmittance, thereby providing a good lithographic property of high resolution.

DETAILED DESCRIPTION OF THE INVENTION

EXAMPLE 1
Synthesis of Monomer

EXAMPLE 1-1

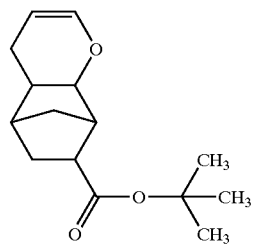

In an autoclave were placed 233 g (1.2 mol) of t-butyl 5-norbomene-2-carboxylate, 22.4 g (0.4 mol) of acrolein, 0.5 g of hydroquinone, followed by sealing, and the mixture was reacted under 20 atmospheric pressure (to be abbreviated as "atm") for 15 hours while maintained at a temperature of 170° C. Here, the hydroquinone serves as a polymerization inhibitor used for suppressing polymerization. Thereafter, the obtained reactant solution was separated under reduced pressure to collect 180 g of unreacted t-butyl 5-norbomene-2-carboxylate by filtration, thereby obtaining 45 g of a final desired product 3-oxa-tricyclo[6.2. 1.0$^{2,7}$] undec-4-ene-10-carboxylate at a 45% yield based on acrolein.

In Example 1–1, [4+2]Diels-Alder cyclo-additions were used for reaction between a norbomene derivative and an acrolein derivative, under reaction conditions of 20 atm pressure and 170° C. temperature. However, a pressure in the range of 15 to 100 atm and a temperature in range of 150 to 250° C. can also be applied. If the reaction pressure is increased, the same yield of the desired product can be obtained at a relatively lower temperature of approximately 150° C.

EXAMPLE 1-2

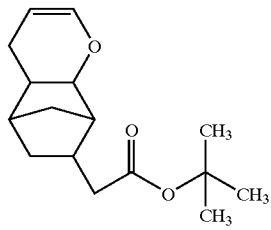

250 g of t-butyl 5-norbornene-2-acetate and 22.4 g of acrolein were reacted in the same manner as in Example 1–1 to synthesize a desired product. As a result, 51 g of t-butyl 3-oxa-tricyclo[6.2.1.0$^{2,7}$]ndec-4-ene-10-carboxylate was obtained.

EXAMPLE 1-3

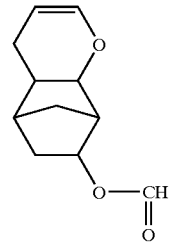

248 g of 5-norbomene-2-yl formate and 33.6 g of acrolein were reacted in the same manner asin Example1-1to synthesize adesired product. As aresult, 57 g of 3-oxa-tricyclo [6.2.1.0$^{2,7}$]undec-4-ene-10-yl formate was obtained.

EXAMPLE 1-4

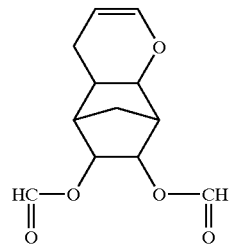

218 g of 5-norbomene-2,3-yl diformate and 22.4 g of acrolein were reacted in the same manner as in Example 1–1 to synthesize a desired product. As a result, 47 g of 3-oxa-tricyclo[6.2.1.0$^{2,7}$]undec-4-ene-9,10-yl diformate was obtained.

EXAMPLE 1–5

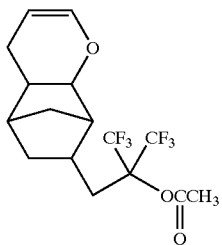

284 g of 3-(5-bicyclo[2.2.1]hepten-2-yi)-1,1,1-trifluoro-2-(trifluoromethyl)-2-propyl acetate and 16.8 g of acrolein were reacted in the same manner as in Example 1–1 to synthesize a desired product. As a result, 56 g of 3-(3-oxa-tricyclo[6.2.1.0$^{2,7}$]undec-4-ene-10-yl)-1,1,1-trifluoro-2-(trifluoromethyl)-2-propyl acetate was obtained at a 85% yield.

EXAMPLE 2
Synthesis of Polymer

EXAMPLE 2–1

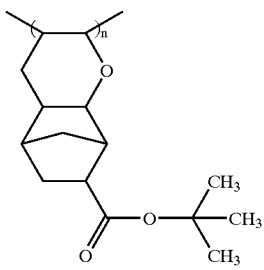

25.0 g of the monomer obtained in Example 1–1 was dissolved in 100 g of anhydrous dichloromethane, and then bubbling was conducted with nitrogen for 2 hours to then be maintained in a nitrogen atmosphere.

The obtained reactant was cooled to −30° C., and a solution prepared by diluting 0.14 g of $BF_3$ as a polymerization catalyst in 5 g of ethyl ether was slowly added thereto dropwise to be polymerized for 2 hours. 5.0 g of methanol was added to the resultant product. The resultant product was dissolved in an excess methanol solution (10 fold), and the precipitate was dissolved in THF again and then reprecipitated with a methanol solution. The obtained precipitate was filtered, and dried in a vacuum oven at 50° C. for 24 hours, thereby obtaining a desired product at a 75% yield.

The weight average molecular weight (Mw) and polydispersity (Mw/Mn) of the obtained product were 11,000 and 1.9, respectively.

In Example 2–1, cationic polymerization was used and $BF_3$ was used as a polymerization catalyst. However, another polymerization catalyst such as $BCl_3$, $BBr_3$, trifluoroacetic acid, iodine, hydrogen iodide/iodine or alkyl aluminum can be used instead of $BF_3$. In addition to dichloromethane, usable polymerization solvents include cyclohexane, ethyl ether, hexane and dichloroethane. The polymerization temperature in range of −80 to 0° C. can be applied.

EXAMPLE 2–2

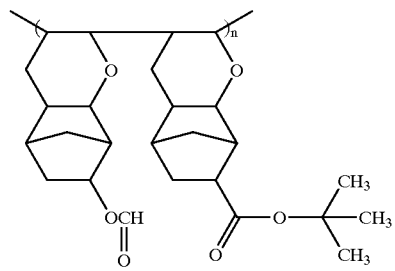

12.5 g of the monomer obtained in Example 1–1 and 9.7 g of the monomer obtained in Example 1–3 were polymerized in the same manner as in Example 2–1 and purified to obtain a desired product at a 73% yield.

EXAMPLE 2–3

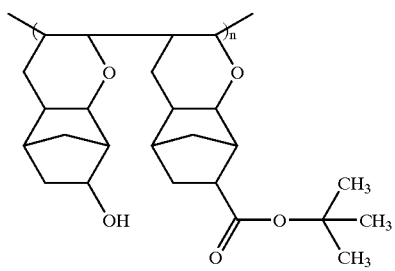

15.0 g of the polymer obtained in Example 2–2 was poured into a 100 ml TBF solution and methanol mixed in a ratio of 1:1, 5.0 g of 28% aqueous ammonia was added thereto, and refluxed for 5 hours.

The obtained reaction product was cooled to room temperature and neutralized by adding a 10% HCl solution dropwise thereto, followed by precipitation in excess water (10 fold). The obtained precipitate was dissolved in THF again and reprecipitated in a methanol solution. The resultant precipitate was filtered and dried in a vacuum oven at 50° C. for 24 hours, thereby obtaining a desired product at a 85% yield.

EXAMPLE 2–4

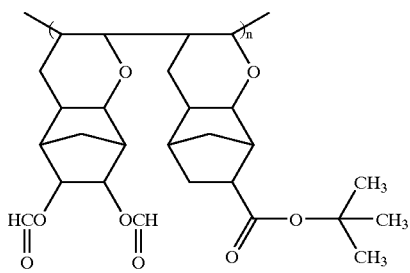

12.5 g of the monomer obtained in Example 1–1 and 11.9 g of the monomer obtained in Example 1–4 were polymerized in the same manner as in Example 2–1 and purified to obtain a desired product at a 68% yield.

EXAMPLE 2-5

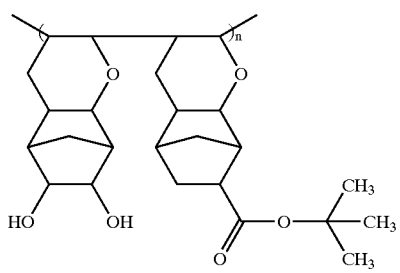

The polymer obtained in Example 2–4 was hydrolyzed in the same manner as in Example 2–3 and purified to obtain a desired product at a 88% yield.

The weight average molecular weight (Mw) and polydispersity (Mw/Mn) of the obtained product were 11,000 and 1.9, respectively.

EXAMPLE 2-6

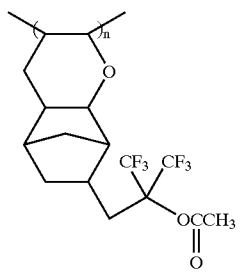

37.2 g of the monomer obtained in Example 1–5 was polymerized in the same manner as in Example 2-1 and purified to obtain a desired product at a 72% yield.

EXAMPLE 2-7

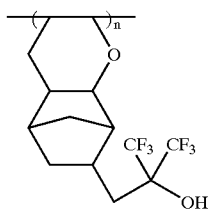

The polymer obtained in Example 2–6 was poured into a 100 ml TBF solution and methanol mixed in a ratio of 1:1, 5.0 g of 28% aqueous ammonia was added thereto, and refluxed for 5 hours.

The obtained reaction product was cooled to room temperature and neutralized by adding a 10% HCl solution dropwise thereto, followed by precipitation in excess water (10 fold). The obtained precipitate was dissolved in THF again and reprecipitated in a methanol solution. The resultant precipitate was filtered and dried in a vacuum oven at 50° C. for 24 hours, thereby obtaining a desired product at a 88% yield.

EXAMPLE 2-8

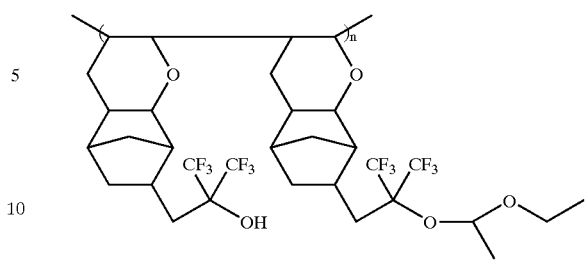

10 g of the polymer obtained in Example 2–7 was dissolved in a dichloromethane solution, and then 5.0 g of ethyl vinyl ether and 0.5 g of toluenesulfonic acid were poured into the obtained solution and reacted at room temperature for about 3 hours. Thereafter, the resulting product was precipitated in excess water. The obtained precipitate was dissolved in THF and then reprecipitated with a methanol solution. The obtained precipitate was filtered, and dried in a vacuum oven at 50° C. for 24 hours, thereby obtaining a desired product.

The weight average molecular weight (Mw) and polydispersity (Mw/Mn) of the obtained product were 10,100 and 1.74, respectively.

EXAMPLE 2-9

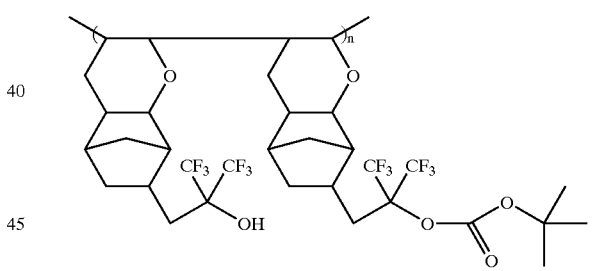

0.61 g of sodium hydride (60% solution dispersed in mineral oil) was poured into 60 ml THF and then the obtained mixture solution was cooled to 0° C. A solution prepared by dissolving 10 g of the polymer obtained in Example 2–7 in a 50 ml THF solution was slowly added to the mixture solution dropwise, followed by adding a 20 ml THF solution containing 2.8 g of di-t-butyl dicarbonate. The resultant product was reacted at room temperature for one day and then unreacted sodium hydride was quenched with ice. The reaction product was evaporated to remove the solvent under reduced pressure to obtain a 50 ml solution, and then precipitated in excess water. The obtained precipitate was dissolved in THF again and then reprecipitated with water. The obtained precipitate was filtered, and dried in a vacuum oven at 50° C. for 24 hours, thereby obtaining a desired product.

EXAMPLE 2-10

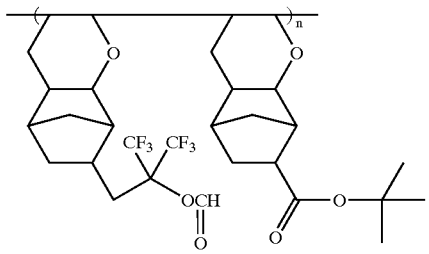

12.5 g of the monomer obtained in Example 1–1 and 18.6 g of the monomer obtained in Example 1–5 were polymerized in the same manner as in Example 2-1 and purified to obtain a desired product at a 70% yield.

EXAMPLE 2-11

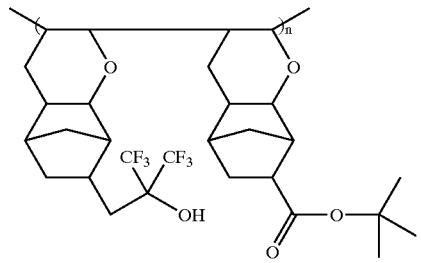

The polymer obtained in Example 2–10 was hydrolyzed in the same manner as in Example 2–7 and purified to obtain a desired product at a 85% yield.

EXAMPLE 2-12

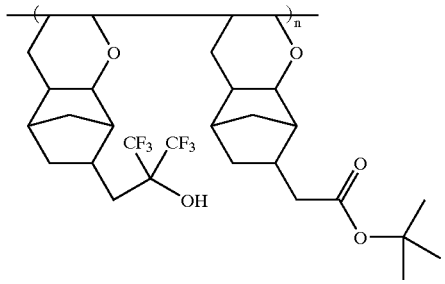

26.4 g of the monomer obtained in Example 1–2 and 18.6 g of the monomer obtained in Example 1–5 were polymerized in the same manner as in Example 2-1 and purified to obtain a polymer at a 65% yield. Then, the obtained polymer was hydrolyzed in the same manner as in Example 2–7 and purified to obtain a desired product at a 83% yield.

EXAMPLE 2-13

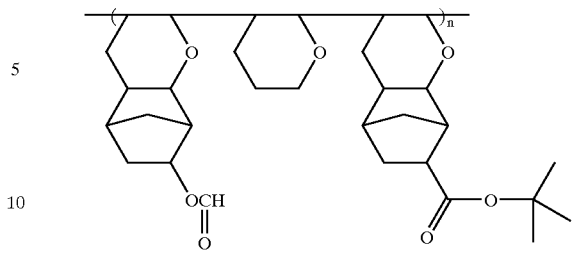

8.7 g of the monomer obtained in Example 1–1, 6.7 g of the monomer obtained in Example 1–3 and 3.0 g of dihydropyran were polymerized in the same manner as in Example 2-1 and purified to obtain a desired polymer at a 82% yield.

EXAMPLE 2-14

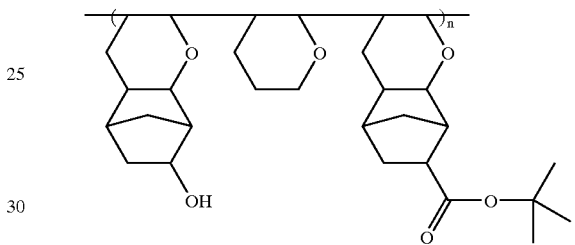

The polymer obtained in Example 2–13 was hydrolyzed in the same manner as in Example 2–7 and purified to obtain a desired product at a 85% yield.

EXAMPLE 2-15

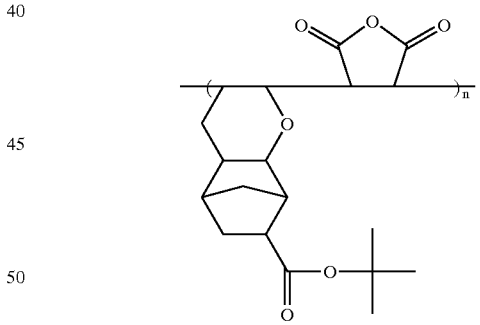

4.9 g of maleic anhydride and 7.5 g of the monomer obtained in Example 1–1 were dissolved in 12 g of anhydrous THF and then 0.82 g of azobisisobutyronitrile (AIBN) was added thereto. Thereafter, degassing was performed three times by a freeze-pump thaw method and the resultant product was polymerized at 65° C. for 24 hours.

After completion of the reaction, the obtained resultant product was precipitated in an excess isopropyl alcohol solution (10 fold). The obtained precipitate was dissolved in THF again and then reprecipitated with an isopropyl alcohol solution. The obtained precipitate was filtered, and dried in a vacuum oven at 50° C. for 24 hours, thereby obtaining a desired product at a 85% yield.

EXAMPLE 2-16

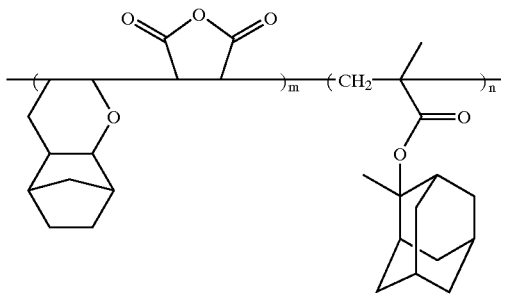

4.5 g of 3-oxa-tricyclo[6.2.1.0,$^{2,7}$]undec-4-ene, 3.0 g of maleic anhydride and 9.4 g of 2-methyl-2-adamantyl methacrylate were dissolved in 12 g of THF and then 0.82 g of AIBN was added thereto. Thereafter, degassing was performed and the resultant product was polymerized at 65° C. for 24 hours.

After completion of the reaction, the obtained resultant product was precipitated in an excess isopropyl alcohol solution (10 fold). The obtained precipitate was dissolved in THF again and then reprecipitated with an isopropyl alcohol solution. The obtained precipitate was filtered, and dried in a vacuum oven at 50° C. for 24 hours, thereby obtaining a desired product at a 83% yield.

The weight average molecular weight (Mw) and polydispersity (Mw/Mn) of the obtained product were 9,500 and 2.1, respectively.

EXAMPLES 2-17

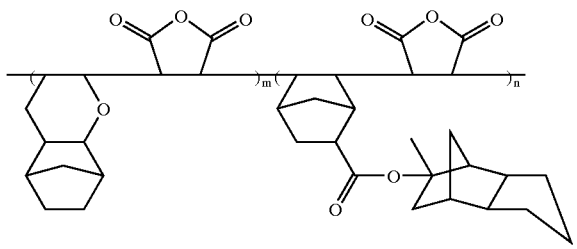

Polymerization was carried out in the same manner as in Example 2-16 using 4.5 g of 3-oxa-tricyclo[6.2.1.0$^{2,7}$] undec-4-ene, 6.0 g of maleic anhydride and 11.5 g of 8-methyl-8-tricyclo[5.2.1.0$^{2,7}$]decanyl-5-norbornene-2-carboxylate (MTCDNC), followed by purification, thereby obtaining a desired polymer at a 76% yield.

The weight average molecular weight (w) and polydispersity (Mw/Mn) of the obtained product were 8,000 and 2.3, respectively.

EXAMPLE 3

Preparation of Resist Composition and Lithographic Performance

Resist compositions were prepared by completely dissolving 1.0 g of polymers synthesized in Examples 2-1 through 2-17, 0.02 g of triphenylsulfonium trifluoromethane sulfonate (triflate) as a PAG and 2 mg of triisodecylamine as an organic base in 8.0 g of cyclohexanone and then filtering using a 0.2 μm membrane filter. Si wafers treated by organic anti-reflective coating (ARC) were coated with the obtained resist compositions to a thickness of about 0.3 μm.

Thereafter, the resultant wafers were soft-baked at 120° C. for 90 seconds, and then exposed using an ArF excimer laser stepper (NA=0.6), followed by performing PEB at 120° C. for 90 seconds.

Then, the resultant products were developed using a 2.38 wt % tetramethyl ammonium hydroxide (TMAH) solution for about 60 seconds to form resist patterns.

As a result, resolutions of 0.15 μm line-and-space patterns were obtained at exposure doses of 10 to 30 mJ/cm$^2$.

Since the photosensitive polymer according to the present invention basically includes multi-ring alkenyl ether, it has excellent resistance to dry etching. Also, since the photosensitive polymer according to the present invention includes a pyran ring structure in its backbone, it has superb adhesive property to underlying layers. Further, since polymers can be synthesized in a simple manner, monomers having various structures can be prepared using various norbornene derivatives being widely used as polymers for forming photoresists, and various copolymers can be easily obtained according to requirements.

In particular, whereas a heavy metal catalyst is used for polymerization of norbornene derivatives known as having excellent resistance to dry etching in the prior art, unavoidably resulting in contamination of resist compositions using the norbornene derivatives, making common use of the conventional resist compositions impossible, photosensitive polymers according to the present invention are prepared by cationic polymerization, thereby providing a multi-ring backbone structure without contamination due to a heavy metal catalyst.

Also, the photosensitive polymer constituting the resist composition according to the present invention can be applied to various kinds of light sources including KrF excimer lasers (248 nm), ArF excimer lasers (193 nm) and F$_2$ excimer lasers (157 nm). In particular, in the case of using the F$_2$ excimer lasers having a wavelength of 157 nm, the resist composition according to the present invention can minimize or remove the use of a functional group having poor transmittance, such as a phenyl group or carboxyl group, and can be provided with a fluorinated hydrocarbon containing group having superb transmittance at 157 nm by a simple substitution method. Therefore, superior transmittance and a good lithographic property of high resolution can be provided.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A monomer having a structure represented by the following formula:

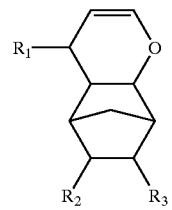

wherein R$_1$ is -H or -CH$_3$, R$_2$ and R$_3$ is selected from the group consisting of -H, -OH, an alkyl group having 1-20 carbon atoms, hydroxyalkyl, alkyloxy, carboxyl, carbonyl, ester and fluorinated alkyloxy.

2. The monomer according to claim 1, having a structure represented by the following formula:

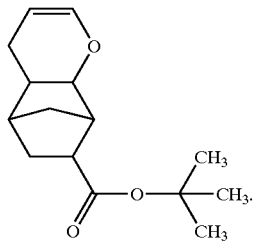

3. The monomer according to claim 1, having a structure represented by the following formula:

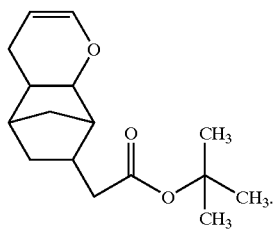

4. The monomer according to claim 1, having a structure represented by the following formula:

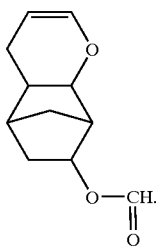

5. The monomer according to claim 1, having a structure represented by the following formula:

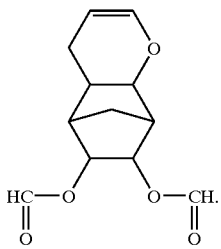

6. The monomer according to claim 1, having a structure represented by the following formula:

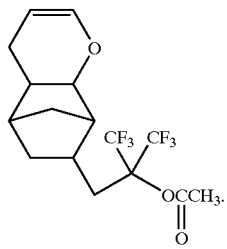

7. A photosensitive polymer comprising a monomer unit represented by the following formula:

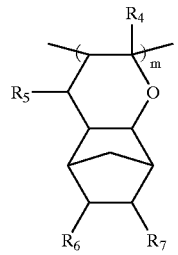

wherein R4 and $R_5$ are -H or -$CH_3$, and $R_6$ and $R_7$ is selected from the group consisting of -H, -OH, an alkyl group having 1–20 carbon atoms, hydroxyalkyl, alkyloxy, carboxyl, carbonyl, ester and fluorinated alkyloxy.

8. The photosensitive polymer according to claim 7, having a structure represented by the following formula:

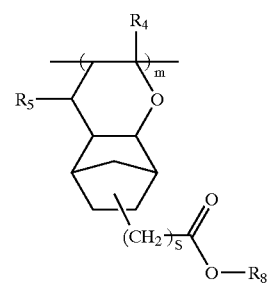

wherein $R_8$ is an alkyl group having 4–12 carbon atoms, and s is an integer from 0 to 2.

9. The photosensitive polymer according to claim 8, wherein $R_8$ is one of t-butyl tetrahydropyranyl or a substituted or unsubstituted alicyclic group having 6 to 12 carbon atoms.

10. The photosensitive polymer according to claim 9, wherein $R_8$ is selected from a group consisting of 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[$5.2.1.0^{2,6}$]decanyl, 8-ethyl-8-tricyclo[$5.2.1.0^{2,6}$]decanyl, 2-methyl-2-adamantyl, 2-ethyl-2-adamantyl, I -adamantyl- I -methylethyl, 2-methyl-2-fenchyl or 2-ethyl-2-fenchyl.

11. The photosensitive polymer according to claim 8, having a structure represented by the following formula:

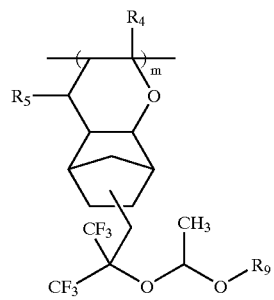

wherein $R_9$ is an alkyl group having 1–20 carbon atoms.

12. The photosensitive polymer according to claim 11, wherein $R_9$ is selected from a group consisting of methyl, ethyl, t-butyl and cyclohexyl.

13. The photosensitive polymer according to claim 8, having a structure represented by the following formula:

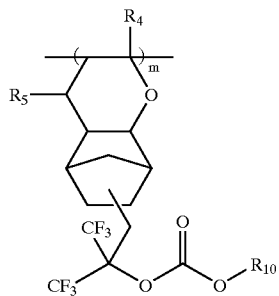

wherein $R_{10}$ is an alkyl group having 1–20 carbon atoms.

14. The photosensitive polymer according to claim 13, wherein $R_{10}$ is selected from a group consisting of methyl, ethyl, t-butyl and cyclohexyl.

15. The photosensitive polymer according to claim 8, having a structure represented by the following formula:

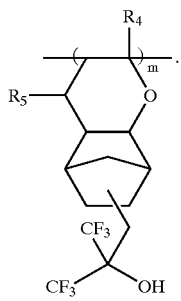

16. A photosensitive polymer having a structure represented by the following formula:

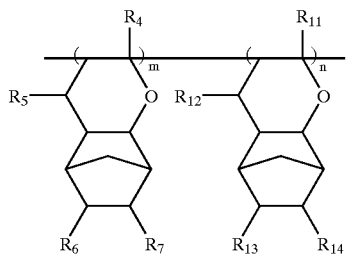

wherein $R_4$, $R_5$, $R_{11}$ and $R_{12}$ are -H or -$CH_3$, $R_6$, $R_7$, $R_{13}$ and $R_{14}$ is selected from the group consisting of -H, -OH, alkyl group having 1–30 carbon atoms hydroxyalkyl, alkyloxy, carboxyl, carbonyl, ester and fluorinated alkyloxy, at least one of $R_6$, $R_7$, $R_{13}$ and $R_{14}$ is an acid-labile group, and m/(m+n) is from about 0.1 to 0.9.

17. The photosensitive polymer according to claim 16, having a structure represented by the following formula:

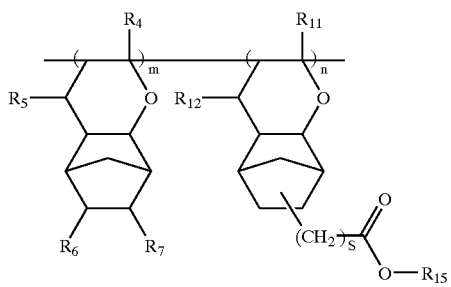

wherein $R_{15}$ is an alkyl group having 4–12 carbon atoms and s is an integer from 0 to 2.

18. The photosensitive polymer according to claim 17, wherein $R_{15}$ is selected from a group consisting of t-butyl, a tetrahydropyranyl and a substituted or unsubstituted alicyclic hydrocarbon group having 6–12 carbon atoms.

19. The photosensitive polymer according to claim 18, wherein $R_{15}$ is selected from a group consisting of 1-methyl-1-cyclohexyl, 1a-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$ ]decanyl, 8-ethyl-8-tricyclo[5 .2. 1.0$^{2,6}$] decanyl, 2-methyl-2-adamantyl, 2-ethyl-2-adamantyl, 1-adamantyl-11-methylethyl, 2-methyl-2-fenchyl and 2-ethyl-2-fenchyl.

20. The photosensitive polymer according to claim 18, having a structure represented by the following formula:

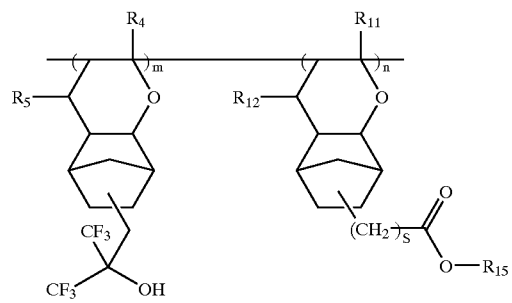

wherein $R_{15}$ is an acid-labile $C_4$~$C_{12}$ hydrocarbon group and s is an integer from 0 to 2.

21. The photosensitive polymer according to claim 18, having a structure represented by the following formula:

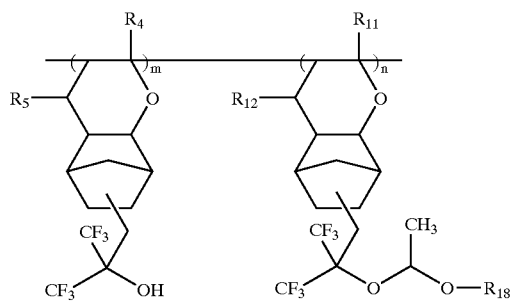

wherein $R_{16}$ is an alkyl group having 1–20 carbon atoms.

22. The photosensitive polymer according to claim 21, wherein $R_{16}$ is selected from a group consisting of methyl, ethyl, t-butyl and cyclohexyl.

23. The photosensitive polymer according to claim 18, having a structure represented by the following formula:

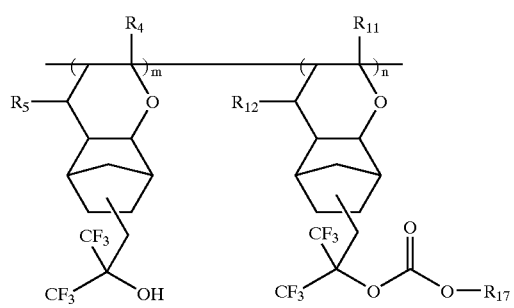

wherein $R_{17}$ is an alkyl group having 1–20 carbon atoms.

24. A photosensitive polymer comprising a polymerized product of (a) at least one monomer unit having a structure represented by the following formula:

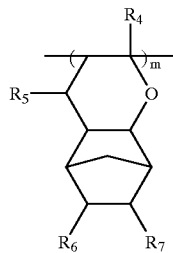

wherein $R_4$ and $R_5$ are -H or -$CH_3$, $R_6$ and $R_7$ is selected from the group consisting of -H, -OH, an alkyl group having 1–20 carbon atoms, hydroxyalkyl, alkyloxy, carboxyl, carbonyl, ester and fluoinated alkyloxy, and (b) at least one comonomer selected from the group consisting of a maleic anhydride monomer, an acrylate monomer, a methacrylate monomer, a norbomene monomer, a dihydrofliran monomer and a dihydropyran monomer.

25. The photosensitive polymer according to claim 24, wherein the comonomer is a dihydrofuran monomer and a dihydropyran monomer unit having a structure represented by the following formula:

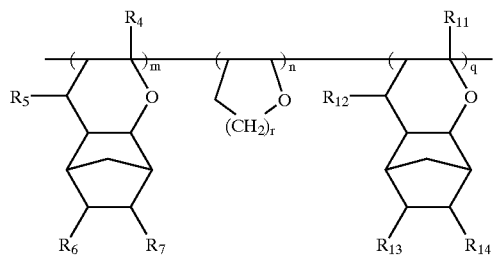

wherein r is 1 or 2, $R_{11}$ and $R_{12}$ are -H or -$CH_3$, $R_{13}$ and $R_{14}$ are -H, -OH or an alkyl group having 1–2 carbon atoms, at least one of $R_6$, $R_7$, $R_{13}$ and $R_{14}$ is an acid-labile group, m/(m+n+q) is from about 0.1 to 0.8, n/(m+n+q) is from about 0.1 to 0.8, and q/(m+n+q) is from about 0.1 to 0.8.

26. The photosensitive polymer according to claim 25, having a structure represented by the following formula:

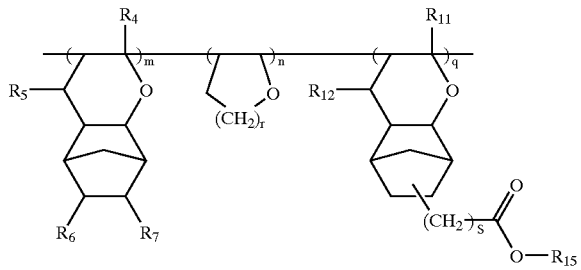

wherein $R_5$ is an acid-labile alkyl group having 4–12 carbon atoms, and s is an integer of from 0to 2.

27. The photosensitive polymer according to claim 26, wherein $R_5$ is selected from a group consisting of t-butyl, tetrahydropyranyl and a substituted or unsubstituted alicyclic hydrocarbon group having 6–12 carbon atoms.

28. The photosensitive polymer according to claim 27, wherein $R_{15}$ is selected if from a group consisting of 1-methyl-1-cyclohexyl, 1-ethyl-1-cyclohexyl, 2-methyl-2-norbornyl, 2-ethyl-2-norbomyl, 2-methyl-2-isobomyl, 2-ethyl-2-isobomyl, 8-methyl-8-tricyclo[$5.2.1.0^{2,6}$]decanyl, 8-ethyl-8-tricyclo[$5.2.1.0^{2,6}$]decanyl, 2-methyl-2-adamantyl, 2-ethyl-2-adamantyl, 1-adamantyl-1-methylethyl, 2-methyl-2-fenchyl and 2-ethyl-2-fenchyl.

29. The photosensitive polymer according to claim 25, having a structure represented by the following formula:

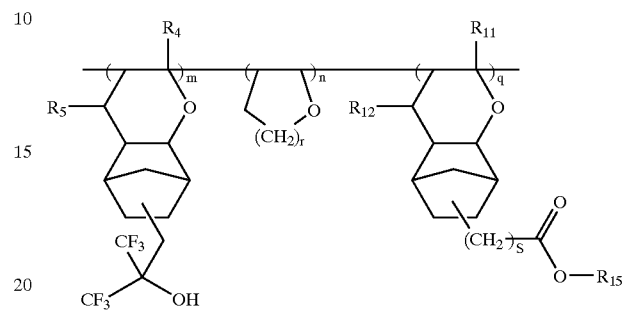

wherein $R_{15}$ is an alkyl group having 4–12 carbon atoms and s is an integer from 0 to 2.

30. The photosensitive polymer according to claim 25, having a structure represented by the following formula:

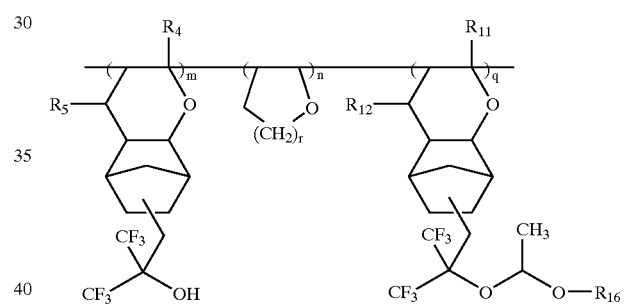

wherein $R_{16}$ is an alkyl group having 1–20 carbon atoms.

31. The photosensitive polymer according to claim 30, wherein $R_{16}$ is selected from a group consisting of methyl, ethyl, t-butyl and cyclohexyl.

32. The photosensitive polymer according to claim 25, having a structure represented by the following formula:

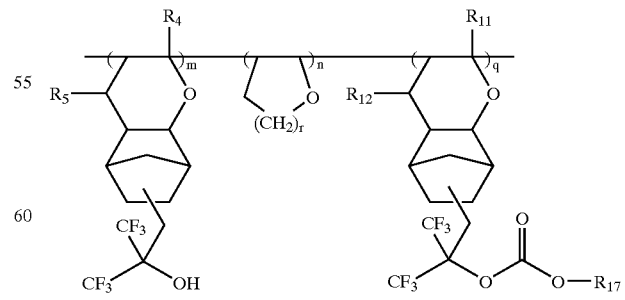

wherein $R_{17}$ is an alkyl group having from 1–20 carbon atoms.

33. The photosensitive polymer according to claim 24, wherein the comonomer unit is a maleic anhydride monomer and has a structure represented by the following formula:

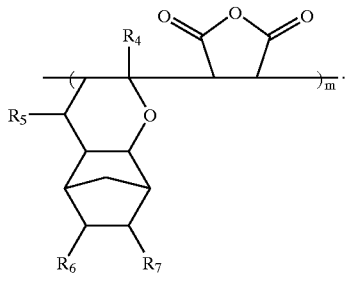

34. The photosensitive polymer according to claim 33 having a structure represented by the following formula:

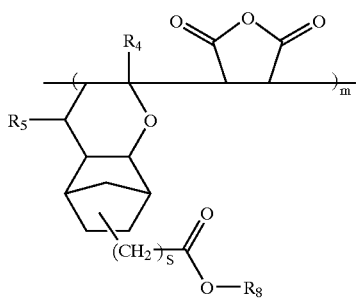

wherein $R_8$ is an alkyl group having 4–12 carbon atoms and s is an integer of from 0 to 2.

35. The photosensitive polymer according to claim 33, having a structure represented by the following formula:

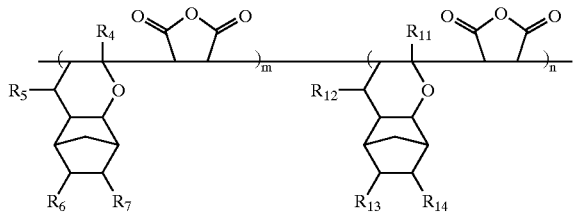

wherein $R_{11}$ and $R_{12}$ are -H or -CH$_3$, $R_{13}$ and $R_{14}$ are -H, -OH or an alkyl group, at least one of $R_6$, $R_7$, $R_{13}$ and $R_{14}$ includes an acid-labile group, m/(m+n) is in the range of 0.1 to 0.9, and n/(m+n) is in the range of 0.1 to 0.9.

36. The photosensitive polymer according to claim 35, having a structure represented by the following formula:

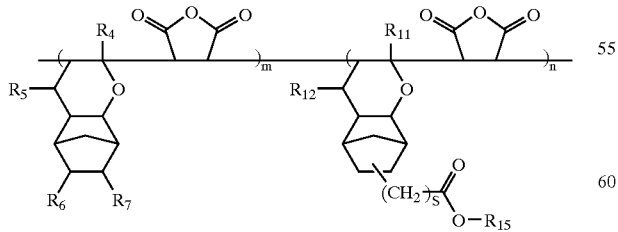

wherein $R_{15}$ is an acid-labile $C_4$~$C_{12}$ hydrocarbon group and s is an integer in the range of 0 to 2 both inclusive.

37. The photosensitive polymer according to claim 24, wherein the comonomer unit includes a maleic anhydride monomer unit and an acrylate or methacrylate monomer unit, and has a structure represented by the following formula:

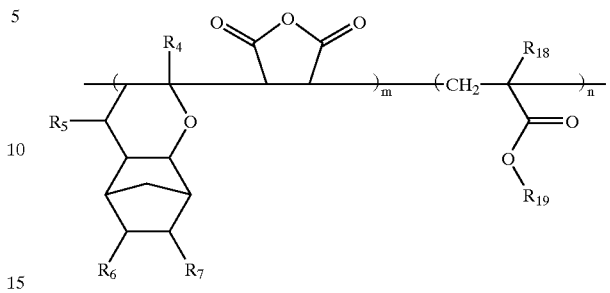

wherein $R_{18}$ is -H or -CH$_3$, $R_{19}$ is an acid-labile group, m/(m+n) is in the range of 0.1 to 0.9, and n/(m+n) is in the range of 0.1 to 0.9.

38. The photosensitive polymer according to claim 24, wherein the comonomer unit includes a maleic anhydride monomeric group and a norbornene monomer group, and has a structure represented by the following formula:

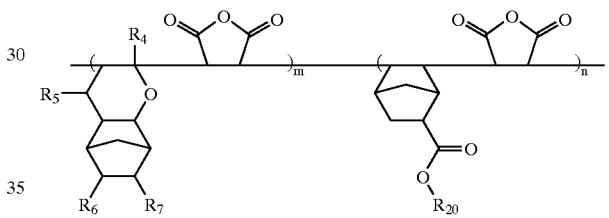

wherein $R_{20}$ is an acid-labile group, m/(m+n) is from about 0.1 to 0.8, and n/(m+n) is from about 0.1 to 0.8.

39. A resist composition comprising:

(a) a photosensitive polymer having a structure represented by the following formula:

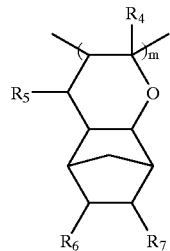

wherein $R_4$ and $R_5$ are -H or -CH$_3$, and $R_6$ and $R_7$ is selected from the group consisting of -H, -OH, an alkyl group having from 1–20 carbon atoms; and (b) a photoacid generator (PAG).

40. The resist composition according to claim 39, wherein the photosensitive polymer has a structure represented by the following formula:

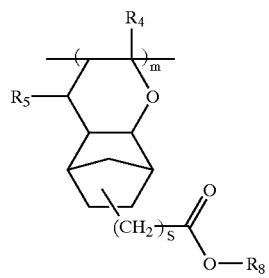

wherein $R_8$ is an alkyl group having 4 to 12 carbon atoms and s is an integer of from 0 to 2.

41. The resist composition according to claim 40, wherein $R_8$ is selected from a group consisting of t-butyl, tetrahydropyranyl and a substituted or unsubstituted alicyclic group having 6–12 carbon atoms.

42. The resist composition according to claim 41, wherein $R_8$ is selected from a group consisting of 1-methyl-1-cyclohexyl, 1-ethyl-1-cyclohexyl, 2-methyl-2-norbornyl, 2-ethyl-2-norbornyl, 2-methyl-2-isobornyl, 2-ethyl-2-isobornyl, 8-methyl-8-tricyclo[5.2.1.0$^{2,6}$]decanyl, 8-ethyl-8-tricyclo[5.2.1.0$^{2,6}$]decanyl, 2-methyl-2-adamantyl, 2-ethyl-2-adamantyl, 1-adamantyl- I -methylethyl, 2-methyl-2-fenchyl and 2-ethyl-2-fenchyl.

43. The resist composition according to claim 39, wherein the photosensitive polymer has a structure represented by the following formula:

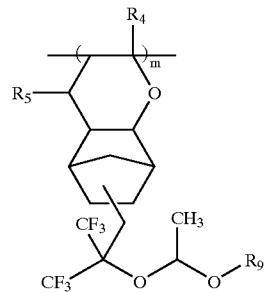

wherein $R_9$ is an alkyl group having 1–20 carbon atoms.

44. The resist composition according to claim 43, wherein $R_9$ is selected from a group consisting of a methyl, ethyl, t-butyl and cyclohexyl.

45. The resist composition according to claim 43, wherein the photosensitive polymer has a structure represented by the following formula:

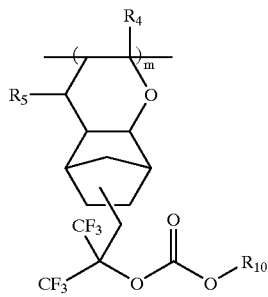

wherein $R_{10}$ is an alkyl group having 1–20 carbon atoms.

46. The resist composition according to claim 43, wherein the photosensitive polymer has a structure represented by the following formula:

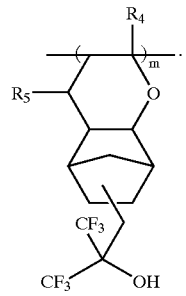

47. The resist composition according to claim 39, wherein the photosensitive polymer has a structure represented by the following formula:

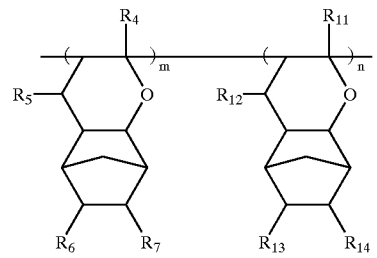

wherein $R_{11}$ and $R_{12}$ are -H or -CH$_3$, RI$_3$ and $R_{14}$ are -H, -OH or an alkyl group having 1–30 carbon atoms, and $R_6$, $R_7$, $R_{13}$ or $R_{14}$ are an acid-labile group and m/(m+n) is from about of 0.1 to 0.9.

48. The resist composition according to claim 47, wherein the photosensitive polymer has a structure represented by the following formula:

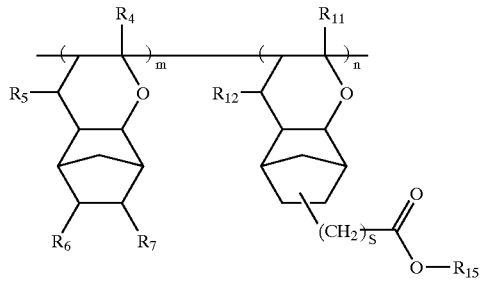

wherein $R_{15}$ is an alkyl group having 4–12 carbon atoms, and s is from 0 to 2.

49. The resist composition according to claim 47, wherein the photosensitive polymer has a structure represented by the following formula:

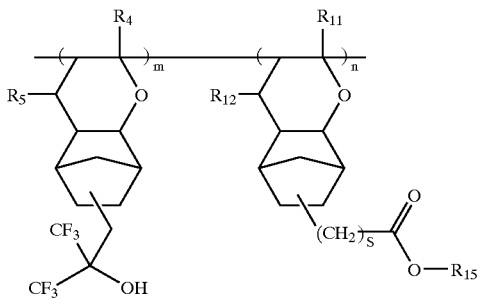

wherein $R_{15}$ is an alkyl group having 4–12 carbon atoms, and s is from 0 to 2.

50. The resist composition according to claim 47, wherein the photosensitive polymer has a structure represented by the following formula:

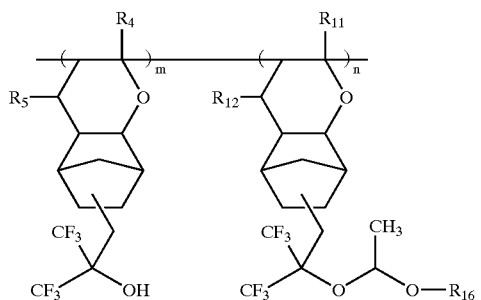

wherein $R_{16}$ is an alkyl group having 1–20 carbon atoms.

51. The resist composition according to claim 47, wherein the photosensitive polymer has a structure represented by the following formula:

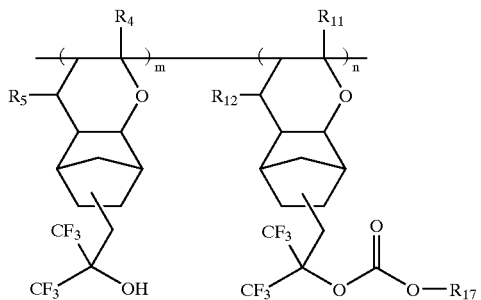

wherein $R_{17}$ is an alkyl group having 1–20 carbon atoms.

52. The resist composition according to claim 47, wherein the weight average molecular weight of the photosensitive polymer is from about 3,000 to 100,000.

53. The resist composition according to claim 47, wherein the amount of the PAG is from about 1 to 30 wt % based on the weight of the photosensitive polymer.

54. The resist composition of claim 47, wherein the PAG comprises a triarylsulfonium salt, a diaryliodonium salt, a sulfonate, or mixtures thereof.

55. The resist composition of claim 54, wherein the PAG comprises triphenylsulfonium triflate, triphenylsulfonium antimonate, diphenyliodonium triflate, diphenyliodonium antimonate, methoxydiphenyliodonium triflate, di-t-butyldiphenyliodonium triflate, 2,6-dinitrobenzyl sulfonates, pyrogallol tris(alkylsulfonates), N-hydroxysuccinimide triflate, norbornene-dicarboximide-triflate, triphenylsulfonium nonaflate, diphenyliodonium nonaflate, methoxydiphenyliodonium nonaflate, di-t-butyldiphenyliodonium nonaflate, N-hydroxysuccinimide nonaflate, norbornene-dicarboximide-nonaflate, PFOS (triphenylsulfonium perfluorooctanesulfonate), diphenyliodonium PFOS, methoxydiphenyliodonium PFOS, di-t-butyldiphenyliodonium triflate, N-hydroxysuccinimide PFOS, norbornene-dicarboximide PFOS, or mixtures thereof.

56. The resist composition of claim 47, further comprising an organic base.

57. The resist composition of claim 56, wherein the amount of the organic base is 0.01–2.0 wt % on the basis of the weight of the photosensitive polymer.

58. The resist composition of claim 56, wherein the organic base comprises a tertiary amine compound alone or a mixture of at least two tertiary amine compounds.

59. The resist composition of claim 56, wherein the organic base comprises triethylamine, triisobutylamine, triisooctylamine, triisodecylamine, diethanolamine, triethanolamine, N-alkyl substituted pyrrolidinone, N-alkyl substituted caprolactam, N-alkyl substituted valerolactam, or a mixture thereof.

60. The resist composition of claim 47, further comprising about 30 to 200 ppm of a surfactant.

61. A resist composition comprising:

(a) a photosensitive polymer comprising a polymerized product of (i) at least one monomer unit having a structure represented by the following formula:

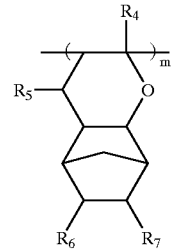

wherein $R_4$ and $R_5$ are -H or -$CH_3$, R and $R_7$ are -H, -OH or an alkyl group having 1–20 carbon atoms, and (ii) at least one comonomer selected from the group consisting of a maleic anhydride monomer, an acrylate monomer, a methacrylate monomer, a norbornene monomer, and dihydrofuiran or dihydropyran monomer; and (b) a PAG.

* * * * *

UNITED STATES PATENT AND TRADEMARK OFFICE
CERTIFICATE OF CORRECTION

PATENT NO.    : 6,713,228 B2
DATED         : March 30, 2004
INVENTOR(S)   : Kim et al.

It is certified that error appears in the above-identified patent and that said Letters Patent is hereby corrected as shown below:

Title page,
Item [57], ABSTRACT,
Line 16, "-CH$_3$, and R$_4$ are" should read -- -CH3, and R$_7$ are --.

Column 2,
Line 62, "4000 A or less." should read -- 4000 Å or less. --.

Column 5,
Line 14, "wherein R4 and" should read -- wherein R$_4$ and --.
Line 14, "are -H1 -OH or" should read -- are -H, -OH or --.
Line 42, "2-norbomyl, 2" should read -- 2-norbornyl, 2 --.
Line 43, "2-isobomyl, 2" should read -- 2-isobornyl, 2 --.
Line 44, "2-isobomyl, 8" should read -- 2-isobornyl, 8 --.

Column 6,
Line 20, "and cyclohexyl," should read -- and cyclohexyl. --.

Column 8,
Line 41, "a norbomene monomer," should read -- a norbornene monomer, --.
Line 63, "and R1$_4$ are" should read -- and R$_{14}$ are --.

Column 11,
Line 39, "wherein R$_8$ is –H" should read -- wherein R$_{18}$ is -H --.

Column 12,
Line 44, "a norbomene monomer," should read -- a norbornene monomer--.
Line 60, "norbomene-dicarboximide" should read -- norbornene-dicarboximide --.
Line 64, "norbomene-dicarboximide" should read -- norbornene-dicarboximide --.

Column 13,
Line 1, "norbomene-dicarboximide" should read -- norbonene-dicarboximide --.
Lines 54 and 62, "5-norbomene-2" should read --5-norbornene-2--.
Line 67, "a norbomene derivative" should read -- a norbornene derivative --.

UNITED STATES PATENT AND TRADEMARK OFFICE
CERTIFICATE OF CORRECTION

PATENT NO. : 6,713,228 B2  
DATED : March 30, 2004  
INVENTOR(S) : Kim et al.

It is certified that error appears in the above-identified patent and that said Letters Patent is hereby corrected as shown below:

Column 14,
Line 26, "[6.2.1.01$^{2,7}$]ndec-4-ene" should read -- [6.2.1.0$^{2,7}$] undec-4-ene --.
Line 44, "5-norbomene-2-yl" should read -- 5-norbornene-2-yl --.
Line 45, "manner asin Examplel1-1 to" should read -- manner as in Example 1-1 to --.
Line 46, "synthesize adesired product." should read -- synthesize a desired product. --.
Line 46, "As aresult, 57 g" should read --As a result, 57 g --.
Line 63, "5-norbomene-2,3-yl" should read -- 5-norbornene-2,3-yl --.

Column 15,
Line 14, "hepten-2-yi)" should read -- hepten-2-yl) --.
Line 18, "4-ene-1 O-yl)" should read -- 4-ene-10-y1) --.

Column 16,
Line 36, "100 ml TBF solution" should read -- 100 ml THF solution --.
Line 38, "and refiuxed for" should read -- and refluxed for --.

Column 17,
Line 56, "100 ml TBF solution" should read -- 100 ml THF solution --.

Column 21,
Line 16, "[6.2.1.0,$^{2,7}$]" should read -- [6.2.1.0$^{2,7}$] --.
Line 51, "weight (w) and" should read -- weight (Mw) and --.

Column 22,
Line 6, "0.15 µtm line-and-space" should read -- 0.15 µm line-and-space --.
Line 17, "various norbomene derivatives" should read -- various norbornene derivatives --.
Line 21, "of norbomene derivatives" should read -- of norbornene derivatives --.

Column 24,
Line 15, "wherein R4 and R$_5$" should read -- wherein R$_4$ and R$_5$ --.
Line 42, "2-norbomyl," should read -- 2-norbornyl; --.
Line 43, "2-isobomyl," should read -- 2-isobornyl, --.
Line 44, "2-isobomyl, 8" should read -- 2-isobornyl, 8 --.
Line 46, "adamantyl, I -adamantyl- I -methylethyl," should read -- adamantyl, 1-adamantyl-l-methylethyl, --.
Line 48, "claim 8, having" should read -- claim 7, having --.

UNITED STATES PATENT AND TRADEMARK OFFICE
CERTIFICATE OF CORRECTION

PATENT NO.    : 6,713,228 B2
DATED         : March 30, 2004
INVENTOR(S)   : Kim et al.

It is certified that error appears in the above-identified patent and that said Letters Patent is hereby corrected as shown below:

Column 25,
Line 1, "claim 8, having" should read -- claim 7, having --.
Line 19, "claim 8, having" should read -- claim 7, having --.
Line 46; "-CH3, R6, $R_7$," should read -- -CH3, $R_6$, $R_7$, --.
Line 47, "-OH, alkyl group" should read -- -OH, an alkyl group --.

Column 26,
Line 7, "cyclohexyl, 1 a-ethyl" should read --cyclohexyl, 1-ethyl--.
Line 8, "2-norbomyl, 2" should read -- 2-norbornyl, 2 --.
Line 11, "adamantly-l1-methylethyl," should read -- adamantyl-l-methylethyl, --.
Lines 13, 31 and 51, "claim 18, having" should read -- claim 16, having --.

Column 27,
Line 19, "and fluoinated alkyloxy," should read -- and fluorinated alkyloxy, --.
Line 22,"a norbomene monomer," should read -- a norbornene monomer, --.
Line 22, "a dihydrofliran monomer" should read -- a dihydrofuran monomer --.
Line 59, "wherein $R_5$ is an" should read -- wherein $R_{15}$ is an --.
Line 60, "of from 0to 2." should read -- of from 0 to 2. --.
Line 62, "wherein $R_5$ is selected" should read -- wherein $R_{15}$ is selected --.
Line 66, "selected if from" should read -- selected from --.

Column 28,
Line 1, "2-ethyl-2-norbomyl," should read -- 2-ethyl-2-norbornyl, --.
Line 1, "2-methyl-2-isobomyl," should read -- 2-methyl-2-isobornyl, --.
Line 2, "2-ethyl-2-isobomyl," should read -- 2-ethyl-2-isobornyl, --.

Column 30,
Line 64, "atoms; and" should read -- atoms, hydroxyalkyl, alkyloxy, carboxyl, carbonyl, ester and fluorinated alkyloxy; and --.

Column 31,
Line 32, "2-ethyl-2-norbomyl," should read -- 2-ethyl-2-norbornyl, --.
Line 35, "1-adamantyl- I -methylethyl," should read -- 1-adamantyl-l-methylethyl, --.
Line 65, "claim 43, wherein" should read -- claim 39, wherein --.

Page 3 of 4

UNITED STATES PATENT AND TRADEMARK OFFICE
CERTIFICATE OF CORRECTION

PATENT NO.   : 6,713,228 B2
DATED        : March 30, 2004
INVENTOR(S)  : Kim et al.

It is certified that error appears in the above-identified patent and that said Letters Patent is hereby corrected as shown below:

Column 32,
Line 15, "claim 43, wherein" should read -- claim 39, wherein --.
Line 46, "-$CH_3$, R and" should read ---$CH_3$, $R_{13}$ and --.

Column 34,
Line 11, "norbomene-dicarboximide" should read -- norbornene-dicarboximide --.
Line 15, "norbomene-dicarboximide" should read -- norbornene-dicarboximide --.
Line 21, "is 0.01-2.0 wt %" should read -- is 0.01~2.0 wt % --.
Line 53, "-$CH_3$, R and" should read -- -$CH_3$, $R_6$ and --.
Line 57, "a norbomene monomer," should read -- a norbornene monomer, --.
Line 57, "and dihydrofuiran or" should read -- and dihydrofuran or --.

Signed and Sealed this

Twenty-eighth Day of September, 2004

JON W. DUDAS
*Director of the United States Patent and Trademark Office*